United States Patent [19]

Davis

[11] Patent Number: 4,789,541

[45] Date of Patent: * Dec. 6, 1988

[54] METHOD AND COMPOSITION FOR IN VIVO RADIOLABELING OF RED BLOOD CELLS WITH $^{99m}$TC

[76] Inventor: Michael H. Davis, 3020 E. Inglewood Ct., Springfield, Mo. 65804

[*] Notice: The portion of the term of this patent subsequent to Sep. 8, 2004 has been disclaimed.

[21] Appl. No.: 62,597

[22] Filed: Jun. 16, 1987

Related U.S. Application Data

[63] Continuation-in-part of Ser. No. 784,020, Oct. 4, 1985, Pat. No. 4,692,324.

[51] Int. Cl.$^4$ .................... A61K 43/00; A61K 49/02; A61K 49/00; G01N 33/15
[52] U.S. Cl. ......................................... 424/1.1; 424/9; 422/61
[58] Field of Search .................... 424/1.1, 9, 127, 131; 534/14; 423/476, 494; 422/61

[56] References Cited

U.S. PATENT DOCUMENTS

| | | | |
|---|---|---|---|
| 4,075,314 | 2/1978 | Wolfangel et al. | 424/1.1 |
| 4,113,850 | 9/1978 | Benes | 424/1.1 |
| 4,300,569 | 11/1981 | Bonneau | 424/1.1 |
| 4,342,740 | 8/1982 | Narra et al. | 424/1.1 |

OTHER PUBLICATIONS

Patel et al., J. Nuclear Medicine, vol. 20 (8), pp. 877–881 (1979).
Prince et al., J. Nuclear Medicine, vol. 21 (8), pp. 763–766 (1980).

Primary Examiner—John F. Terapane
Assistant Examiner—J. E. Thomas
Attorney, Agent, or Firm—Finnegan, Henderson, Farabow, Garrett & Dunner

[57] ABSTRACT

A composition containing stannous chloride and potassium perchlorate is suitable for oral administration to a patient for tinning red blood cells of the patient in vivo prior to labeling the red blood cells with radioactive $^{99m}$Tc. The composition is useful for preparing a patient for blood pool imaging, and especially for carrying out equilibrium gated cardiac imaging.

26 Claims, No Drawings

METHOD AND COMPOSITION FOR IN VIVO RADIOLABELING OF RED BLOOD CELLS WITH $^{99m}$TC

CROSS-REFERENCE TO RELATED APPLICATION

This application is a continuation-in-part of application Ser. No. 784,020, filed Oct. 4, 1985 now U.S. Pat. No. 4,692,324, the entire disclosure of which is relied upon and incorporated by reference herein.

BACKGROUND OF THE INVENTION

This invention relates to radiopharmaceuticals and their use in nuclear medicine. More particularly, this invention relates to a method and composition for labeling red blood cells (RBC) by orally administering a stannous-containing compound to a patient to tin the cells in vivo followed by labeling the RBC with radioactive $^{99m}$Tc. This invention is particularly applicable to tests designed to image blood pools in a patient, and especially for function studies involving the heart using $^{99m}$Tc-labeled red blood cells as the radiopharmaceutical.

Radiopharmaceuticals approved for general distribution and in vivo diagnosis can be used for imaging, organ flow studies, organ function studies, organ localization and dilution and excretion tests. Radiolabeling of red blood cells and their clinical and research applications in nuclear medicine constitute areas of continued interest and steady growth. Significant advances have been made so that at the present time radiolabels with sufficient in vitro and in vivo stability are available for diverse applications. $^{99m}$Tc-labeled red blood cells have revolutionized the field of cardiovascular nuclear medicine by making possible the imaging of blood pools and the non-invasive evaluation of various heart parameters with minimum radiation dose and trauma to the patient. $^{99m}$Tc-RBC are also used for detecting vascular malformations.

It is thought that technetium in the form of technetium pertechnetate moves in and out of the red blood cell but is not bound firmly to the cell in this chemical form. Reduced technetium, on the other hand, does not generally cross the cell membrane but does bind irreversibly with hemoglobin or other red cell components. It is also thought that binding can be achieved by reduction of the pertechnetate once within the cell, and stannous (Sn$^{2+}$) compounds are the most widely used reducing agents for this purpose. In most of the current procedures, red blood cells, generally in whole blood, are contacted with stannous ions using a suitable tin (II) preparation, such as pyrophosphate, glucoheptonate, DTPA, citrate or chloride. This procedure is known as "tinning" the red blood cells and can be carried out in vitro or in vivo.

Protocols for labeling red blood cells with $^{99m}$Tc by in vitro methods typically involve withdrawing a blood sample from a patient, incubating the sample with a tin-containing composition, separating the serum by centrifugation, mixing a portion of the RBC with $^{99m}$Tc pertechnetate, incubating the RBC and injecting the resulting $^{99m}$Tc labeled RBC into the patient. The in vitro methods are characterized by several disadvantages. They require centrifugation to separate the plasma, involve multiple transfers of red blood cells, include a number of handling steps and require multiple venous punctures with the concomitant risks of tissue and vascular damage, infection and discomfort to the patient. In vitro methods frequently require the services of a skilled technician.

In vivo methods for labeling red blood cells with $^{99m}$Tc are based on the intravenous administration of a suitable amount of stannous ion to a patient followed by an in vivo incubation period, typically about 30 minutes. This is followed by the intravenous injection of $^{99m}$Tc pertechnetate. While RBC labeling occurs almost immediately, the process requires two injections. Once again, multiple venous punctures increase the discomfort to the patient and raise the risk of infection and damage to the biologic systems.

Combination of the in vivo and in vitro methods has been proposed. The combined method is essentially an in vivo "tinning" procedure, wherein (Sn II) is intravenously injected into the patient, followed by withdrawal of a blood sample, incubation of the sample with $^{99m}$Tc-pertechnetate to label red blood cells in vitro and reinjection of the resulting labelled RBC in plasma to the patient. While the combined in vivo-in vitro method is said to improve labelling efficiency and the subsequent imaging process, the method suffers some of the same disadvantages previously described for the in vivo method, the most serious being the requirement for multiple intravenous punctures and the complexity of the various manipulations required.

The in vitro, in vivo and combined in vitro-in vivo methods for labeling red blood cells require costly stannous chloride solutions having limited shelf-life. The existing methods also require costly and relatively complicated equipment to successfully label RBC for clinical studies.

Accordingly, there exists a need in the art for a simple, less costly and effective method and composition for radiolabelling red blood cells with $^{99m}$Tc. The method should not require a centrifugation step for separating plasma from RBC. The method should be conducted in vivo to minimize technician time and eliminate the multiplicity of sample-handling steps required in the in vitro methods. The need for costly and complicated equipment should be minimized. In addition, the requirement for venous punctures should be reduced in order to minimize tissue and vascular damage in the patient and to lessen patient discomfort and the risk of infection. The method and composition should provide high uptake of $^{99m}$Tc by red blood cells and be suitable for carrying out blood pool imaging studies. There should be minimal deposit of the radionuclide in background tissue that may obscure definition of a targeted blood pool organ, such as the heart. The composition should be stable and have a longer shelf-life than stannous chloride preparations for intravenous use.

SUMMARY OF THE INVENTION

Accordingly, this invention aids in fulfilling these needs in the art by providing a drug for use in an improved method for radiolabeling red blood cells and especially for use in carrying out blood pool imaging studies in a patient. In particular, this invention provides a composition consisting essentially of (1) about 10 mg to about 200 mg stannous chloride, and (2) about 250 mg to about 1000 mg potassium perchlorate. The composition can optionally include a pharmaceutically acceptable carrier and can be packaged in the form of a kit.

This invention also provides a method of treating a patient for tinning red blood cells in vivo. The method comprises orally administering to the patient about 8.7 mg/kg body weight to about 42 mg/kg body weight of the composition of the invention and waiting for a time sufficient for $Sn^{2+}$ to be absorbed by red blood cells.

In addition, a method is provided for radiolabeling red blood cells of a patient having RBC tinned in accordance with the invention, wherein the patient's tinned red blood cells are contacted with $^{99m}Tc$ and the cells are incubated for a time sufficient to radiolabel the cells.

There is also provided a method of carrying out equilibrium blood pool imaging in a patient having red blood cells labeled according to the method of the invention.

The stannous-containing composition of this invention is intended for oral administration to the patient. Patient treatment is thereby simplified and less time consuming than the intravenous mode of administration previously used. Demands for technician time and the associated expense are thus reduced. Oral administration also increases patient acceptance and reduces patient discomfort, the risk of extravasation and the risk of infection when compared with the intravenous administration of stannous compounds heretofore used. This invention additionally improves imaging by improving target-to-background ratio, which makes it possible to reduce radiation dose, expense of the radiopharmaceutical used and potential radiation hazards.

DETAILED DESCRIPTION

The composition of this invention is suitable for "tinning" red blood cells of the patient in vivo prior to labeling the RBC with radioactive $^{99m}Tc$. The composition of this invention contains stannous chloride and potassium perchlorate for this purpose.

Stannous chloride can be employed in any water soluble, non-toxic form. For example, the composition can include $SnCl_2$ or $SnCl_2 \cdot 2H_2O$. Tin chloride dihydrate (i.e., $SnCl_2 \cdot 2H_2O$) is preferred because it can be readily formulated in solid dosage form to provide a drug having good shelf-life. In addition, the dihydrate is believed to be less irritating to the gastrointestinal tract than anhydrous stannous chloride. The stannous chloride should preferably be of pharmaceutical quality.

Oral administration of stannous chloride alone is unsatisfactory because of high gastric uptake of $Sn^{2+}$. Administration of $^{99m}Tc$ after oral administration of $Sn^{2+}$ results in unacceptably high levels of the radiolabel in the gastrointestinal tract. This occurs even if the radiolabel is intravenously administered to the patient after oral administration of the stannous chloride. Deposition of the radionuclide in the gut, which constitutes the background when imaging the heart and other vital organs, obscures definition of the targeted blood pool organ. For example, in blood pool imaging of the heart, this unwanted imaging of the gut results in overlap of the stomach with the heart thereby obscuring heart borders. In addition, there is unwanted loss of the radionuclide into other organs that are not of clinical interest. Accordingly, it has been discovered that the composition of the invention must also contain potassium perchlorate ($KClO_4$). The potassium perchlorate should preferably be of pharmaceutical quality.

The composition of this invention consists essentially of about 10 mg to about 200 mg of the stannous chloride (anhydrous form) and about 250 mg to 1000 mg potassium perchlorate. Stannous chloride is employed in an amount sufficient for tinning red blood cells of a patient in vivo prior to tagging the RBC with the $^{99m}Tc$ radiopharmaceutical so that RBC will be radiolabeled in quantity adequate to carry out a desired clinical or diagnostic test on the patient. The stannous chloride should be employed in the minimum amount necessary for this purpose. The amount of the stannous chloride in the composition is expressed on the basis of the anhydrous form. Thus, larger amounts may be employed if the dihydrate is administered to the patient. Potassium perchlorate is employed in an amount sufficient to substantially inhibit absorption of intravenously administered $^{99m}Tc$ by the gut, while permitting the tinning of RBC and radiolabeling the RBC with the $^{99m}Tc$. Typically, the stannous chloride and potassium perchlorate will be employed in the composition in a weight ratio of about 1:5 to about 1:100, preferably about 1:20 to about 1:30, and especially about 1:24.

A preferred composition for tinning red blood cells in vivo in preparation for equilibrium gated blood pool imaging of the heart in an adult patient of 50 kg or more in body weight consists essentially of 25 mg $SnCl_2 \cdot 2H_2O$ ($\pm 1$ mg) and about 600 mg $KClO_4$ in powder form in a gelatin capsule.

The composition of the invention can be used in mammalian therapy. The mammals that can be treated include humans, as well as animals, such as felines, such as domestic cats, and dogs, guinea pigs, mice, rats, monkeys, pigs, horses and cows. The composition of the invention can be orally administered to the patient either fasting or post-prandially. The dose of the composition administered to the patient is about 8.9 mg/kg body weight to about 42 mg/kg body weight. A preferred dosage is about 8.9 mg/kg to about 10 mg/kg. It will be understood that the dosage will depend upon the nature of the study being conducted, patient size, whether the patient is in fasting or non-fasting state and the rate of absorption by the biologic system. Small dosages are typically employed for small animals and larger doses for humans. Dosages equal to about one-half a normal adult dose can be employed in pediatric applications. Generally, for carrying out equilibrium gated blood pool imaging of the heart, the composition of this invention can be orally administered to a fasting adult patient of 50 kg or more in an amount of about 8.9 mg/kg body weight to about 15 mg/kg body weight, preferably about 8 mg to about 10 mg/kg body weight. There is no known interaction of the composition of the invention with other drugs a patient may take.

The stannous chloride and potassium perchlorate can be combined and together orally administered to the patient or each compound can be separately administered. Preferably, the stannous chloride and potassium perchlorate are administered so that the compounds can be consumed in a single swallow by the patient. In some circumstances it may be desirable to orally administer the potassium perchlorate in a form and under conditions that will permit the potassium perchlorate to line walls of the gut before stannous chloride contacts the walls. This embodiment can be carried out in different ways. For example, the potassium perchlorate can be first orally administered to the patient, and after a brief time interval, the stannous chloride can be orally administered. As another example, the potassium perchlorate and stannous chloride can be administered together with the stannous chloride in a timed release form that will allow the potassium perchlorate to first line the stomach.

The composition and each of the ingredients therein can each be in the form of pills, tablets, capsules or other ingestable forms. The composition and each of its ingredients can each also take the form of powders or sustained-release formulations and the like. The composition of the invention and its ingredients can each be prepared in the form of solutions, suspensions, or emulsions in vehicles conventionally employed for pharmaceutical purposes.

The composition of this invention and each active ingredient can be combined with solid or liquid pharmaceutically acceptable non-toxic carriers, diluents and adjuvants in order to prepare the compositions for use in the treatment of mammals. Such pharmaceutical carriers can be sterile liquids, such as water and oils, including those of petroleum, animal, vegetable or synthetic origin. Typical carriers are peanut oil, soybean oil, mineral oil, sesame oil and the like. Water is a preferred carrier. Saline solutions and aqueous dextrose and glycerol solutions can also be employed as liquid carriers. Suitable pharmaceutical excipients include starch, glucose, lactose, sucrose, gelatine, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. Other suitable pharmaceutical carriers are described in "Remington's Pharmaceutical Sciences" by E. W. Martin. The compositions will contain an effective amount of the active compounds together with a suitable amount of carrier so as to provide the form for proper administration to the host.

The composition of this invention can be packaged in the form of a kit for convenience of availability and ease of use in tinning red blood cells of a patient in preparation for radiolabeling the cells with $^{99m}$Tc. The kit comprises (1) a solid, unit dose of stannous compound consisting essentially of about 10 mg to about 200 mg of stannous chloride sufficient to tin the red blood cells in vivo; and (2) a solid, unit dose of potassium perchlorate in an amount of about 250 mg to about 1000 mg sufficient to substantially inhibit absorption of $^{99m}$Tc by the gut of the patient, while permitting the tinning of RBC and radiolabeling of RBC with $^{99m}$Tc.

The unit doses can conveniently be in the form of tablets or capsules. The unit dosages can be individually sealed in separate compartments, such as a blister package, and easily removed one-by-one from the package. The dose of stannous chloride and the dose of potassium perchlorate can be combined to form a single, solid dose. The kit can include directions for use of the drug contained in the kit.

This invention is carried out with a naturally occurring radionuclide as the radiopharmaceutical. The radionuclide is $^{99m}$Tc, that is technetium in a metastable state formed by the isomeric transition of molybdenum 99. The $^{99m}$Tc must be in a water soluble form and should preferably be of pharmaceutical quality.

The $^{99m}$Tc radiopharmaceutical is commercially available in prepared form, such as in multiple-dose vials. While convenience and low cost are advantages realized by the use of these vials, a major drawback is that the user must mathematically allow for decay and then calculate the volume necessary to ensure withdrawal of the desired amount of activity. When the radiopharmaceutical is received in prepared form, the proper dosage can be determined from the total volume of the liquid at time of delivery, total activity, concentration, date and time of assay or calibration and the specific activity. A suitable source of $^{99m}$Tc is available under the trade name Technekow from Mallinkrodt Chemical Co., of St. Louis, Missouri.

Since $^{99m}$Tc has a relatively short radioactive half-life of only 6.03 hours, the radionuclide can be obtained from a source not ready for immediate use. A radionuclide generator is suitable for this purpose, and $^{99m}$Tc generators are commercially available. The relatively long-lived $^{99}$Mo continually produces through radioactive decay the shorter-lived daughter nuclide $^{99m}$Tc. The parent nuclide is firmly affixed to a support in the generator and the daughter nuclide is separated by elution. Ion exchange media in the generator facilitate this process. Other elution processes, such as distillation, solvent extraction and precipitation can also be employed, but are generally more complex than elution from ion exchange media. The product should be assayed for concentration of daughter nuclide.

Quality assurance testing of the radiolabel should be performed on a regular basis. Molybdenum breakthrough tests should be performed on all generator eluents before administration to the human patient. Aluminum break-through can also be performed to ensure radiochemical purity. Thin-layer chromatography or paper chromatography techniques can be used to identify radiochemical contamination that may be present in the radiopharmaceutical. Chromatography kits for evaluating technetium preparations and containing all materials necessary are commercially available. Ideally, chromatography should be performed before administration of the radiopharmaceutical to the patient. The sterility and apyrogenicity of the $^{99m}$Tc must be assured. Aseptic techniques must be employed for preparation and handling of the radionuclide.

Technetium as pertechnetate can be employed in the invention in the form of a water soluble salt with a non-toxic, pharmaceutically acceptable cation. The preferred source of radionuclide for use in the invention is sodium pertechnetate (Na $^{99m}$TcO$_4$), procured either in prepackaged form or from a $^{99}$Mo/$^{99m}$Tc generator system. When the salt is dissolved in body fluids, a solution is formed in which sodium ions and $^{99m}$Tc$_{O4}^-$ are produced.

The clinically appropriate dose administered to the patient and its consequent radiation dose to vital organs must be determined. The dose can be varied depending upon biologic parameters, such as uptake, distribution, retention and release of the radiopharmaceutical in the body and the fraction of the emitted energy that is absorbed by the target. Precaution should be taken to ensure that the patient does not exceed the maximum permissible dose of radiation for the patient's age group. The dose will also depend upon the nature of the test to be conducted. The amount of $^{99m}$Tc administered in practicing this invention is typically about 0.2 mCi per kg to about 0.43 mCi/kg of the patient's body weight, preferably about 0.2 mCi/kg to about 0.29 mCi/kg body weight. For conducting an equilibrium gated blood pool imaging study of the heart, a dosage of about 0.25 mCi per kg body weight has been found to be suitable.

The radionuclide can assume various forms. The radionuclide can be in the form of a liquid containing a known concentration of $^{99m}$Tc, the activity of the dose depending on the time of administration and the volume used. A liquid $^{99m}$Tc-containing composition is normally compounded with water or normal saline solution as the vehicle. The agent can be a true solution of soluble compounds or complexes, or there may be colloidal or suspended particles of varying sizes.

The process of adherence of the radiolabel to the red blood cell is time dependent; adherence is a function of the length of time $Sn^{2+}$ ion is in the milieu of the cell and the time of incubation of the $^{99m}$Tc radiolabel with the cell. Incubation of stannous ion in vivo is carried out for a time sufficient for stannous ion in the composition of the invention to tin red blood cells in the patient and accumulate in the patient's blood pool.

The resulting tinned red blood cells are incubated with $^{99m}$Tc for a time sufficient for the radiolabel to bind to red blood cells, which then accumulate in the blood pool without substantial binding of radioactive technetium to cells in the gut of the patient. If incubation is carried out in vivo, the $^{99m}$Tc must be administered before there is appreciable clearance of stannous ion from the biologic system. While the $^{99m}$Tc can be intravenously administered to the patient when the stannous compound is orally administered, this normally results in loss of the isotope, which is cleared by the kidney while RBC are being tagged. For this reason, incubation of the tinned cells with the $^{99m}$Tc radiolabel is generally commenced about 10 to about 120 minutes, preferably about 20 to about 60 minutes, after oral administration of the SnCl$_2$. An incubation time of about 30 minutes following oral dosing of the stannous compound has been found to be sufficient before administration of $^{99m}$Tc in preparation for equilibrium gated blood pool imaging of the heart.

In the preferred method of this invention, the $^{99m}$Tc is intravenously administered to the patient following oral administration of the composition of the invention. A high percentage of red blood cells are thus radiolabelled.

While intravenous administration of $^{99m}$Tc is preferred, it will be understood that the red blood cells tinned in vivo according to the invention can also be incubated with $^{99m}$Tc by the known in vitro techniques or the modified in vivo/in vitro techniques. For example, the composition of this invention can be orally administered to a patient. After incubating in vivo for a time sufficient to tin red blood cells, such as 30 minutes, a blood sample is drawn and anticoagulated by thorough mixing with heparin (10 ml) in a syringe. $^{99m}$Tc is incubated in the syringe of blood for 10 to 20 minutes, and then the blood sample is reinjected into the patient. Equilibrium blood pool imaging can then be carried out. In any event, oral administration of the composition of this invention replaces the intravenous administration of SnCl$_2$ required in prior techniques.

The composition and method of this invention make it possible to efficiently and safely radiolabel red blood cells. The efficiency of radionuclide uptake by red blood cells compared to plasma (i.e. "labeling yield") is at least about 85% and generally at least about 90% in this invention. Preferably, labeling yield is about 95% to about 97% or more. When the labeling yield is at least about 85%, there is adequate delineation of targeted blood pool organs for imaging.

Labeling yield is determined by assaying a sample according to the following technique. A 10 ml sample of whole blood is withdrawn from the patient and the sample is immediately centrifuged at 800 g for 7 minutes. Plasma is separated from blood. A sufficient amount of normal saline is added to the sample to give a total volume of 8 ml. In the same geometric tube, each fraction is assayed in a gamma counter subtracting background counts from each. Hematocrit is measured. Labeling yield can then be calculated using the following equation:

$$\text{Labeling Yield} = \frac{\text{Red Cell Gamma Count}}{\text{Plasma Gamma Count}} \times 100 \times \frac{1-\text{Hematocrit}}{\text{Hematocrit}}.$$

Radioactivity is determined as of 45 minutes following dosing of the $^{99m}$Tc. Measurements on samples after longer lag times can be adjusted for radioactive decay. Studies on canines have shown that red blood cells can be tagged using the composition and method of this invention with a labeling yield of about 95 to about 98%, which is equal to the efficiency obtained with in vitro and in vivo methods.

Studies on canines have also demonstrated that stannous chloride in the dosage of this invention can be safely administered and that there is rapid clearance of tin from the circulatory system. For example, 1000 mg of stannous chloride dihydrate were administered to canines having body weights of 12 to 15 kg. A blood sample was drawn from each host one hour after administration. The serum was assayed for tin content by atomic spectroscopy with a sensitivity of 0.1 microgram per deciliter. Tin was undetectable indicating rapid clearance from the circulatory system even at very high dosages.

The composition of this invention makes it possible to reduce the dose of the radionuclide to the patient. Because there is a reduction in the loss of the radiolabel by uptake in non-targeted organs, a smaller dose of $^{99m}$Tc can be employed and the teratogenic effects from radiation exposure possibly reduced.

This invention can be employed for any in vivo radionuclide diagnostic or therapeutic method requiring the presence or use of $^{99m}$Tc labeled red blood cells. This invention is preferably employed for radiolabeling red blood cells with $^{99m}$Tc in preparation for equilibrium blood pool imaging of biologic systems other than the gut. For example, this invention is useful for imaging the heart and other vital organs in a patient. The invention can be employed for blood pool visualization of spleen, heart, great vessels, aortic bifurcation, testicles and lower extremeties.

This invention is especially useful for conducting an equilibrium multiple gated blood pool imaging study, which is a widely used method for the evaluation of right and left ventricular size and function. Imaging of the cardiac blood pool can be carried out with a resting patient to assess the ventricular ejection fractions, ventricular volumes and regional kinesis of the myocardium. It is also possible to establish the damage done by myocardial infarction and to assess the loss of contractility of the myocardium. Resting patients with valvular disease or other myocardiopathies can also be studied.

The gated equilibrium cardiac blood pool study can also be carried out on patients during or after exercise. Studies of this type are useful in population screening for coronary artery disease, for evaluating patients with mitral or aortic valve disease and to study myocardium function. By administering oral stannous chloride and oral potassium perchlorate to a patient the problem of unwanted uptake of $^{99m}Tc$ in the gut is overcome and this resolves the subsequent problem of overlap between the stomach and the blood pool of vital organs being imaged even when the $^{99m}Tc$ is intravenously administered.

The blood pool study can be carried out with conventional equipment. A scintillation detector can be used to show radionuclide distribution in the body and in its organs, both as a planar imaging system and a tomographic system. Both types of systems can utilize stationary or moving detectors. The imaging devices require collimators and utilize a crystal-photomultiplier assembly. Planar systems can be based on a rectilinear scanner, such as a single detector assembly or multiple detector assembly, or a stationary camera, such as a single crystal camera (scintillation camera or Anger camera) or a multi-crystal stationary imaging device. Scintillation cameras yield X and Y position signals that require ancillary data presentation equipment, such as a cathode ray tube oscilloscope, a multi-format programmer, a variable persistence scope or a whole-body imaging table.

Equilibrium gated cardiac imaging can be carried out using conventional techniques. Cardiac measurements require the combination of a scintillation camera and a properly programmed computer. Red blood cells in the patient are tinned using the composition of this invention as previously described. $^{99m}Tc$ pertechnetate is incubated with the tinned RBC. The initial passage of the tracer through the heart is imaged. Scintographic counts are acquired throughout the cardiac cycle and analyzed in short time intervals. As a general routine in resting studies, a septal left anterior oblique projection and an anterior projection are obtained. The study can be carried out during exercise by placing the patient in a supine position beneath the scintillation camera. Baseline resting studies are recorded. The patient is allowed to begin exercising and to stabilize. Data is recorded for a period of time. The exercise load is increased, and once again the patient is allowed a period to stabilize followed by intervals for recording data. Sequential sets of images can be obtained until the patient reaches a maximum exercise level. The equilibrium gated blood pool imaging study carried out according to this invention produces highly resolved images.

The time of imaging is ideally chosen when the target-to-non-target ratio of radiopharmaceutical is at its maximum. To wait longer would serve no purpose because the best target-to-non-target ratio has already been reached by this time. Delay only results in loss of count rate as a result of decay and biologic clearance. For example, equilibrium gated blood pool imaging is generally initiated about 10 minutes to about 60 minutes following pertechnetate dosing. The accumulation of radiolabeled red blood cells in the heart appears to reach its maximum at about 30 minutes after pertechnetate dosing. Imaging can be carried out over a prolonged time period, if necessary, and for as long as the decay of the radiolabel makes it possible. For instance, equilibrium gated blood pool imaging is generally carried out for about 4 to about 10 minutes. Repeat studies can be performed serially.

This invention will be more fully understood by reference to the following Examples.

EXAMPLE 1

Three mongrel dogs weighing an average of 16 kg each were selected for study. To each dog there was administered 25 mg of hydrous stannous chloride ($SnCl_{12}.2H_2O$; ACS Grade; Aldrich Chemical Co.) and 600 mg potassium perchlorate ($KClO_4$; ACS Grade; Mallinkrodt) peroral. Thirty minutes later each animal received $^{99m}Tc$ (Technekow; Mallinkrodt) in 0.9 normal saline solution administered intravenously via the brachial vein. A blood sample (10 ml) was withdrawn from each animal at 10 and 60 minutes to determine degree of red cell labeling. Plasma was isolated from each sample by centrifugation and radioactivity of the plasma fraction was compared with radioactivity of the red blood cell fraction by measurement in a well counter. Red cell labeling yield was 90 to 95% at 10 minutes and 95 to 98% at 60 minutes.

Blood pool cardiac images were compared with gastric uptake. Gastric uptake of the radiopharmaceutical was negligible. Background interference was also negligible.

EXAMPLE 2

Fifteen randomly selected human patients were referred for study for gated blood pool imaging of the heart. Patients were studied in a non-fasting state. Patient size varied from 69.1–95 kg. in weight.

Each patient received a composition containing 25 mg of stannous chloride dihydrate (ACS Grade; Aldrich Chemical Co.) and 600 mgs of potassium perchlorate ACS Grade; Mallinkrodt) peroral in a single swallow. Thirty minutes later, each patient received 0.25 mCi/kg of $^{99m}Tc$ as sodium pertechnetate in aqueous solution administered intravenously via peripheral upper extremity vein. Ten milliliter aliquots of whole blood were collected from each patient in non-anticoagulant tubes at 10 and 60 minutes after administration of the radiolabel. Each aliquot was immediately centrifuged to separate plasma from red blood cells. Radioactivity of red blood cells and plasma was determined in a well counter and efficiency of red blood cell labeling calculated for the 10 and 60 minute samples.

Views of the heart were obtained with adequate sampling over gastric and spleen regions at 10 to 60 minutes after $^{99m}Tc$ injection. Static views of the region of the salivary and thyroid glands were obtained for qualitative comparison of uptake.

The efficiency of the label was 82 to 99% at the 10 minute interval with a mean of 94%. The efficiency of the label at 60 minutes was 92 to 100% with a mean of 97%.

Gastric uptake was judged to be 0–1+ on an objective scale of 0 to 4+, wherein 0 signifies no uptake in the region, 1+ signifies some uptake and 4+ signifies complete visualization of borders. Sample size was too small for comparison of fasting to non-fasting states. Qualitatively, there was little variation in gastric uptake when compared with the customary in vivo labeling with intravenous stannous chloride. Thyroid and salivary gland uptake, however, was qualitatively estimated to be approximately $\frac{1}{3}$ to $\frac{1}{2}$ that of the customary in vivo labeling techniques with intravenous stannous chloride.

Patients tolerated the oral administration of the composition well. There were no complaints of gastric upset or evidence of gastric irritation following administration.

In summary, this invention provides a simple, less costly and effective method for radiolabeling red blood cells with $^{99m}$Tc. The method does not require a centrifugation step for separating plasma from RBC. The method can be conducted in vivo to minimize technician time and eliminate the multiplicity of sample-handling steps required in the in vitro methods. The need for costly and complicated equipment is minimized. In addition, the requirement for venous punctures is reduced thereby minimizing tissue and vascular damage and discomfort in the patient and lessening the risk of infection. The method and composition provide high uptake of $^{99m}$Tc by red blood cells, and are suitable for carrying out blood pool imaging studies. There is minimal deposit of the radionuclide in background tissue that may obscure definition of a targeted blood pool organ, such as the heart. The composition is stable and has a longer shelf-life than stannous chloride preparations for intravenous use.

What is claimed is:

1. A pill in the form of a tablet or capsule suitable for oral administration to a patient for tinning red blood cells of the patient in vivo in preparation for radiolabeling the red blood cells with $^{99m}$Tc, wherein said pill comprises a composition consisting essentially of
   (1) about 10 mg to about 200 mg stannous chloride, and
   (2) about 250 mg to about 1000 mg potassium perchlorate.

2. A pill according to claim 1, in which the stannous chloride is stannous chloride dihydrate.

3. A pill according to claim 1, wherein said composition contains a pharmaceutically acceptable carrier.

4. A pill according to claim 1, in which the stannous chloride and potassium perchlorate are in a weight ratio of about 1:5 to about 1:100.

5. A pill according to claim 1, in which the stannous chloride and potassium perchlorate are in a weight ratio of about 1:20 to about 1:30.

6. A pill according to claim 1, in which the stannous chloride and potassium perchlorate are in a weight ratio of about 1:24.

7. A pill according to claim 5, wherein said composition contains a pharmaceutically acceptable carrier.

8. A pill according to claim 7, wherein said composition consists essentially of 25 mg SnCl$_2$.2H$_2$O($\pm$1 mg) and about 600 mg KClO$_4$.

9. A method of treating a mammalian patient for tinning red blood cells in vivo, said method comprising
   orally administering to the patient about 8.9 mg/kg body weight to about 10 mg/kg body weight of a composition consisting essentially of
   (1) about 10 mg to about 200 mg stannous chloride, and
   (2) about 250 mg to about 1000 mg potassium perchlorate; and
   incubating red blood cells in vivo for a time sufficient for Sn$^{2+}$ to be absorbed by the red blood cells.

10. Method according to claim 9, wherein the stannous chloride and potassium perchlorate are in a weight ratio of about 1:5 to about 1:100.

11. Method according to claim 9, wherein the stannous chloride and potassium perchlorate are in a weight ratio of about 1:20 to about 1:30.

12. Method according to claim 9, wherein the stannous chloride and potassium perchlorate are in a weight ratio of about 1:24.

13. Method according to claim 9, wherein the red blood cells are incubated in vivo with Sn$^{2+}$ for about 10 minutes to about 120 minutes.

14. Method according to claim 9, wherein the patient is a human.

15. Method according to claim 9, wherein the mammal is a canine or feline.

16. A method for radiolabeling red blood cells of a patient, said method comprising
    orally administering to the patient about 8.9 mg/kg body weight to about 42 mg/kg body weight of a composition consisting essentially of
    (1) about 10 mg to about 200 mg stannous chloride, and
    (2) about 250 mg to about 1000 mg potassium perchlorate;
    incubating red blood cells in vivo in the presence of Sn$^{2+}$ for a time sufficient for tin to be absorbed by the red blood cells in the patient;
    contacting the resulting tinned red blood cells with $^{99m}$Tc; and
    incubating the tinned red blood cells with the $^{99m}$Tc for a time sufficient to radiolabel the cells.

17. Method according to claim 16, wherein the $^{99m}$Tc is intravenously administered to the patient.

18. Method according to claim 17, wherein the $^{99m}$Tc is derived from sodium pertechnetate.

19. Method according to claim 18, wherein the $^{99m}$Tc is administered in an amount of about 0.2 mCi/kg to about 0.43 mCi/kg of the patient's body weight.

20. Method according to claim 19, wherein labeling yield of red blood cells is at least about 90% at 45 minutes after $^{99m}$Tc dosing.

21. A method of carrying out equilibrium blood pool imaging in a patient, said method comprising
    orally administering to the patient about 8.9 mg/kg body weight to about 42 mg/kg body weight of a composition consisting essentially of
    (1) about 10 to about 200 mg stannous chloride, and
    (2) about 250 mg to about 1000 mg potassium perchlorate;
    incubating red blood cells in vivo in the presence of Sn$^{2+}$ for a time sufficient for tin to be absorbed by the red blood cells in the patient;
    contacting the resulting tinned red blood cells with $^{99m}$Tc; and
    incubating the tinned red blood cells with the $^{99m}$Tc for a time sufficient to radiolabel the cells; and
    imaging a blood pool of the patient with means for detecting and reporting radioactivity emitted by the $^{99m}$Tc.

22. A kit for tinning red blood cells of a patient in vivo in preparation for radiolabeling the cells with $^{99m}$Tc, wherein the kit contains a drug consisting essentially of
    (1) a solid, unit dose of stannous compound consisting essentially of about 10 mg to about 200 mg of stannous chloride sufficient to tin the red blood cells in vivo; and
    (2) a solid, unit dose of potassium perchlorate in an amount of about 250 mg to about 1000 mg sufficient to substantially inhibit absorption of $^{99m}$Tc by the gut of a patient, while permitting the tinning of red blood cells and radiolabeling of red blood cells with $^{99m}$Tc;
    wherein the stannous chloride and potassium perchlorate are in a weight ratio of about 1:5 to about 1:100.

23. Kit according to claim 22, wherein each unit dose is in the form of a tablet or capsule.

24. Kit according to claim 23, wherein the tablets and capsules are individually sealed in separate compartments in a package.

25. Kit according to claim 24, wherein the dose of stannous chloride and the dose of potassium perchlorate are combined to form a single, solid dose.

26. Kit according to claim 25, wherein the kit includes directions for use of the drug contained in the kit.

* * * * *